US012308665B2

(12) United States Patent
Fried (10) Patent No.: US 12,308,665 B2
(45) Date of Patent: May 20, 2025

(54) FLEXIBLE RECHARGER WITH INTEGRATED ELECTRONICS

(71) Applicant: Medtronic, Inc., Minneapolis, MN (US)

(72) Inventor: Andrew Thomas Fried, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 960 days.

(21) Appl. No.: 17/394,348

(22) Filed: Aug. 4, 2021

(65) Prior Publication Data

US 2023/0045477 A1 Feb. 9, 2023

(51) Int. Cl.
*H02J 50/00* (2016.01)
*A61N 1/24* (2006.01)
*A61N 1/378* (2006.01)
*H02J 7/00* (2006.01)
*H02J 50/10* (2016.01)
*H02J 50/70* (2016.01)
*H02J 7/02* (2016.01)

(52) U.S. Cl.
CPC ............ *H02J 50/70* (2016.02); *A61N 1/24* (2013.01); *A61N 1/3787* (2013.01); *H02J 7/007192* (2020.01); *H02J 50/005* (2020.01); *H02J 50/10* (2016.02); *A61B 2560/0219* (2013.01); *H02J 7/02* (2013.01)

(58) Field of Classification Search
None
See application file for complete search history.

(56) References Cited

U.S. PATENT DOCUMENTS

| | | | |
|---|---|---|---|
| 8,406,893 B2* | 3/2013 | Krause | A61N 1/3787 607/61 |
| 8,907,531 B2 | 12/2014 | Hall et al. | |
| 9,079,043 B2* | 7/2015 | Stark | H02J 7/00034 |
| 9,461,476 B2 | 10/2016 | Kamata | |
| 9,805,863 B2* | 10/2017 | Hansen | A61N 1/37229 |
| 10,105,103 B2 | 10/2018 | Goldshtein et al. | |
| 10,192,830 B2 | 1/2019 | Rogers et al. | |
| 10,285,760 B2* | 5/2019 | Sadjadi | A61B 34/10 |
| 10,672,530 B2 | 6/2020 | Ronay | |
| 10,686,337 B2 | 6/2020 | Roy et al. | |
| 10,940,251 B2* | 3/2021 | Hansen | H02J 50/12 |
| 11,337,215 B2* | 5/2022 | Park | H04B 5/72 |

(Continued)

*Primary Examiner* — Leigh M Garbowski
(74) *Attorney, Agent, or Firm* — Shumaker & Sieffert, P.A.

(57) ABSTRACT

A wireless power transfer system in which the driver and control circuitry are located within the electromagnetic field of the power transmission antenna, e.g., a charging coil. The power transfer system may be contained in a flexible housing, which change shape using one or more hinges, be formed of a conformable material and so on. Changes in the relative location of the antenna and the circuitry may cause interference in the circuitry and loading of the antenna, which in turn may impact the electromagnetic field output by the antenna. The wireless power system may include sensors that provide an indication of an amount of deformation of the system. The driver circuitry of this disclosure may receive an indication of the relative location of the circuitry to the antenna and compensate for changes in the output electromagnetic field caused by changes in the relative location.

20 Claims, 4 Drawing Sheets

(56) References Cited

U.S. PATENT DOCUMENTS

| | | |
|---|---|---|
| 2012/0053657 A1 | 3/2012 | Parker et al. |
| 2016/0322156 A1 | 11/2016 | Yeh et al. |
| 2017/0054213 A1 | 2/2017 | Singh et al. |
| 2017/0143977 A1* | 5/2017 | Kaib ..................... A61N 1/046 |
| 2018/0280708 A1 | 10/2018 | Escalona et al. |
| 2018/0301923 A1 | 10/2018 | White, II et al. |
| 2019/0190296 A1* | 6/2019 | Paralikar .............. A61N 1/3787 |
| 2019/0229770 A1 | 7/2019 | Khaleghi et al. |
| 2019/0290819 A1 | 9/2019 | Hansen |
| 2020/0015678 A1 | 1/2020 | Li et al. |
| 2024/0097499 A1* | 3/2024 | Fried .................... H02J 50/005 |

\* cited by examiner

FLEXIBLE RECHARGER WITH INTEGRATED ELECTRONICS

TECHNICAL FIELD

The disclosure relates to wireless power transfer, and more particularly, power transfer to charge an electrical energy storage device.

BACKGROUND

Portable electronic devices may be located in locations where providing electrical power via a wired connection to a power source may be difficult. Some portable electronic devices may include a power supply such as a rechargeable battery or some other electrical energy storage device. In other examples, portable electronic devices may not include an internal power supply and instead be configured to directly receive wireless power to operate. Some examples of portable electronic devices may include implantable medical devices. Implantable medical devices may receive wireless power via a transcutaneous power transfer configured to either directly power the device or to recharge the electrical energy storage device.

SUMMARY

In general, the disclosure is directed to a wireless power transfer system in which the driver and control circuitry are located within the electromagnetic field of the power transmission antenna, e.g., a charging coil. Changes in the relative location of the antenna and the circuitry may cause interference in the circuitry and/or loading of the antenna, which in turn may impact the electromagnetic field output by the antenna. The control and/or driver circuitry of this disclosure is configured to receive an indication of the relative location of the circuitry to the antenna and compensate for changes in the output electromagnetic field caused by changes in the relative location by, for example, adjusting the signal to the antenna that generates the electromagnetic field.

In some examples, the antenna and circuitry may be contained in a common flexible housing, e.g., configured to change shape using one or more hinges, or formed of a conformable material. The wireless power system may include one or more sensors that provide an indication of the amount of deformation of the system. Based on the indication of deformation, the system may compensate for the changes caused by changing the loading of the output electromagnetic field due to the relative distance between the antenna and the circuitry or deformation of the antenna itself. In some cases, the system may determine the relative distance, or change in relative distance, between the antenna and the circuitry based on the indication of deformation. In other cases, the deformation of the antenna may change the loading with ferrite materials and associated losses in a ferrite closely coupled to the antenna.

In one example, this disclosure describes a system comprising a charging coil configured to wirelessly charge a secondary device, wherein the system is configured to conform to a surface of an external object; driver circuitry configured to operatively connect to the charging coil; and one or more sensors configured to generate a signal representative of a spatial relationship between at least the driver circuitry and the charging coil, wherein the spatial relationship between at least the driver circuitry and the charging coil changes upon the system conforming to the surface of the external object.

In another example, this disclosure describes a device that includes driver circuitry configured to: operatively connect to an antenna; output a driving signal to the antenna, wherein the driving signal causes the antenna to output an electromagnetic field configured to wirelessly transfer energy to a secondary device and wherein the antenna configured to conform to a surface of an external object; processing circuitry operatively coupled to the driver circuitry, the processing circuitry configured to: receive, from the one or more sensors, the signal representative of a spatial relationship between the driver circuitry and the antenna; control, based on the signal representative of the spatial relationship between the driver circuitry and the charging coil, the driving circuitry to adjust the driving signal to compensate for changes in the spatial relationship between the driver circuitry and the antenna.

In another example, this disclosure describes a method comprising generating, by driver circuitry, a driving signal, wherein the driving circuitry is a component of system configured to conform to a surface of an external object; receiving, by a charging coil, the generated driving signal; generating, by the charging coil and based on the driving signal, an electromagnetic field, wherein the generated electromagnetic field is configured to wirelessly transfer power to a secondary device separate from the charging coil; generating, by one or more sensors a signal representative of a spatial relationship between the driver circuitry and the charging coil, wherein the spatial relationship between at least the driver circuitry and the charging coil changes upon the system conforming to the surface of the external object.

The details of one or more examples of the disclosure are set forth in the accompanying drawings and the description below. Other features, objects, and advantages of the disclosure will be apparent from the description and drawings, and from the claims.

DETAILED DESCRIPTION

Devices, systems, and techniques are described related to a wireless power transfer system in which the driver and control circuitry are located within the electromagnetic field of power transmission antenna, e.g., a charging coil. Changes in the relative location of the antenna to the circuitry may cause changes in the overall impedance of the power transfer system. These changes to the overall impedance may be caused by, for example, interference in the circuitry, which in turn may impact the electromagnetic field output by the antenna. Example control and/or driver circuitry of this disclosure is configured to receive an indication of the relative location of the circuitry compared to the antenna and compensate for changes in the output electromagnetic field caused by changes in the relative location. For example, the processing circuitry may adjust the signal to the antenna that generates the electromagnetic field.

In some examples, the antenna and circuitry of the power transmitting system may be contained in a flexible housing, e.g., a housing that is configured to change shape using one or more hinges or any other material, e.g., flexible material, or linkage enabled change in shape, a housing that is formed of a conformable material (e.g., an elastic material configured to bend and/or stretch to conform to another surface shape). The wireless power transmitting system may include one or more sensors that provide an indication of the amount of deformation of the system. Based on the deformation detected by the one or more sensors, the system may determine the relative distance between the antenna and the circuitry and compensate for the changes caused by changing the loading of the output electromagnetic field. In some examples, the system may directly compensate for the change in deformation without specifically identifying the relative change in distance between the antenna and the circuitry (e.g., using a look up table or formula that specifies a relationship between the conformation status or change and respective target charging parameter(s). For example, the amount of deformation may have a small impact on the AC impedance of the antenna coil itself, but because of the relative distance to the circuitry or other metallic or ferromagnetic materials within the electromagnetic field, the overall system AC impedance may increase or decrease. In some examples, the changes in overall system impedance of the power transmitting system may be a factor in determining an amount of heating in a secondary device, e.g., a device receiving power from the power transmitting system. Some examples of sensors that may be configured to determine an amount of deformation may include strain gauges, pressure sensors, capacitive sensors, or other similar types of sensors.

Figure 1:
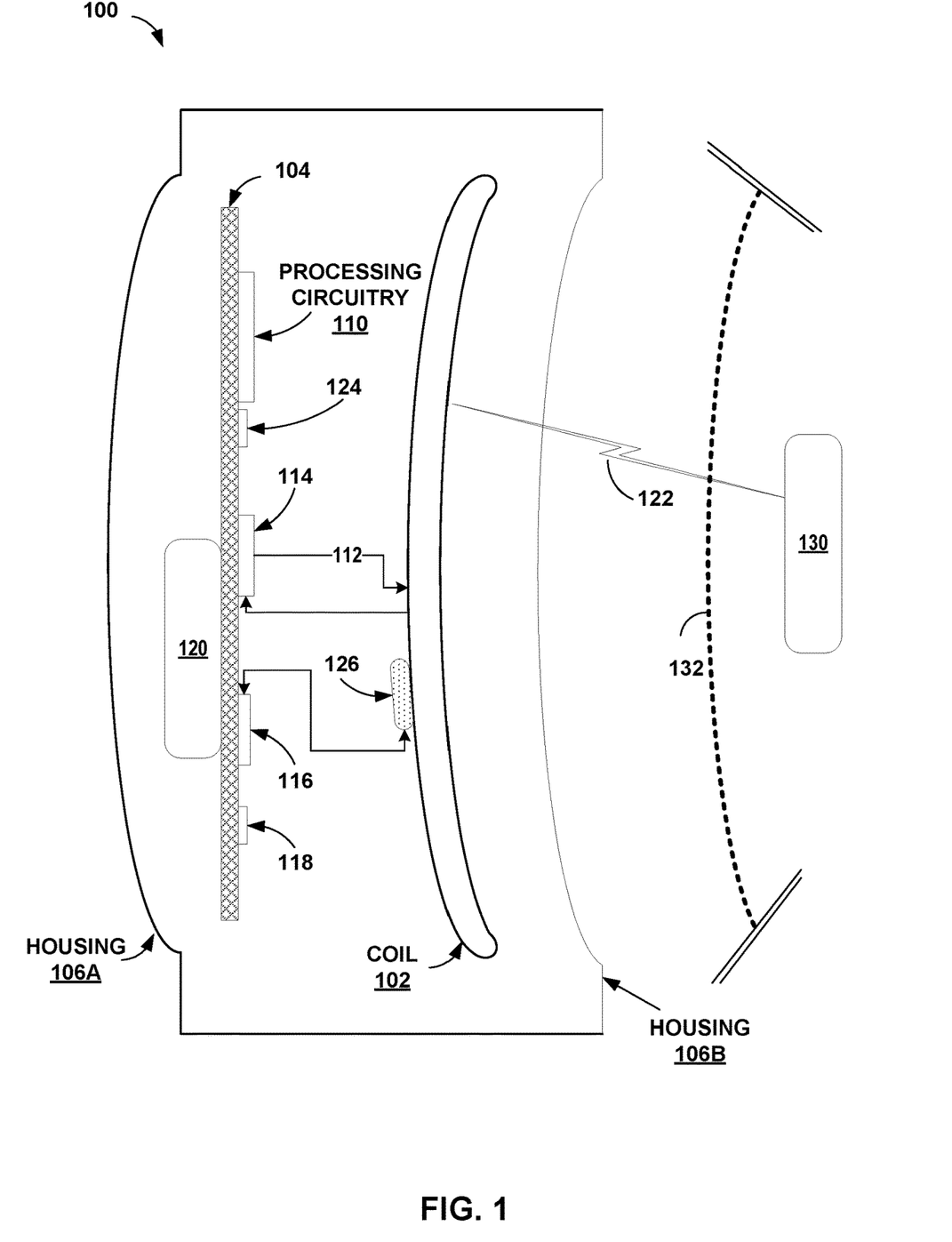
FIG. 1 is a conceptual diagram illustrating a cross-section of an example a wireless power transmitting system including a conformable coil and housing according to one or more techniques of this disclosure.

FIG. 1 is a conceptual diagram illustrating a wireless power transmitting system 100 including a conformable coil and housing according to one or more techniques of this disclosure. System 100 may include a conformable housing comprising a front housing 106A and a back housing 106B that enclose and protect a power transmitting antenna, e.g., coil 102 and circuitry mounted to circuit board 104. In some examples, a system may include the wireless power transmitting system 100 and an implantable medical device (IMD) 130. IMD 130 may receive wireless power through a patient's tissue 132, which may include skin, adipose tissue, muscle tissue and so on, depending upon the location of IMD 130.

In the example of FIG. 1, either or both of front housing 106A and back housing 106B (collectively referred to as housing 106) may be formed using a flexible material configured to conform (e.g., bend and/or stretch) to a surface of an external object. For example, housing 106 may be formed using a type of rubber, plastic, metal, or similar material that may flex to mold around and conform, at least partially, to an object external to housing 106. In some examples, housing 106 may conform to an external object such as a portion of human anatomy such as an ankle, back, buttocks, pectoral region, neck, cranium, and so on. In other examples, system 100 may be mounted in a seat, such as an automobile seat, or a piece of furniture and may conform and flex with the shape of the seat when the seat is occupied, e.g., by a person. A change in the shape of conformable housing 106 may cause a deformation in the shape of coil 102. In some examples, the amount of deformation may change an amount of loading reflected to the driver circuitry via coil 102. The amount of loading may be affected by materials within the electromagnetic field produced by coil 102. Some examples of materials that may affect the electromagnetic field may include metallic materials and ferromagnetic materials.

A change in the shape of conformable housing 106 may also cause a change in the spatial relationship between the circuitry and coil 102. For example, the circuitry and/or coil 102 may be flexible or conformable as well such that the circuitry on circuit board 104 may move to different locations within electromagnetic field 122. This different location within electromagnetic field 122 may increase, decrease, or otherwise change the character of electromagnetic field 122 at the region of the circuitry. Circuitry on circuit board 104 may include processing circuitry 110, driver circuitry 114, memory 124, sensing circuitry 116, other circuitry 118, circuit traces, vias, connection points, and power source 120. In some examples, circuit board 104, as well as one or more components of the circuitry on circuit board 104, may also flex to conform to changes in housing 106, and/or coil 102. In some examples, housing 106 may be substantially flat when in an original state, e.g., an "undeformed" or "resting" state. In other examples, housing 106 may pre-curved, e.g., be formed with a radius when in the original state. In some examples, housing 106, though shown as a cross-sectional two-dimensional view in the example of FIG. 1, may have a three-dimensional (3D), e.g., substantially a 3D paraboloid curvature to help housing 106 conform to a 3D external object, e.g., a human cranium, or similar external object.

Coil 102 is a power transmitting antenna and may be also formed by flexible material configured to conform (e.g., bend in one or more planes) to the shape of housing 106. For example, coil 102 may include several loops of wire enclosed by a flexible material and configured to generate electromagnetic field 122 when driven by the circuitry mounted on circuit board 104. The electromagnetic field may transfer power to a secondary device, e.g., a power receiving unit (PRU), which may also be described as a power receiving device. Examples of secondary devices may include a mobile computing device, a mobile phone, portable audio device, a medical device, including an implantable medical device, and so on.

In the example of FIG. 1, the circuitry mounted on circuit board 104 may be within generated electromagnetic field 122. As the shape of coil 102, and housing 106, changes to conform to the shape of an external object, the relative distance and angle between the circuitry and coil 102 may change.

Processing circuitry 110 may receive inputs from sensing circuitry 116, access and execute instructions and store and retrieve information stored at memory 124, control the operation of driving circuitry 114 and send and receive digital communications, e.g., from the secondary unit, or from another computing device. Examples of processing circuitry 110 may include any one or more of a microcontroller (MCU), e.g. a computer on a single integrated circuit containing a processor core, memory, and programmable input/output peripherals, a microprocessor (μP), e.g. a central processing unit (CPU) on a single integrated circuit (IC), a controller, a digital signal processor (DSP), an application specific integrated circuit (ASIC), a field-programmable gate array (FPGA), a system on chip (SoC) or equivalent discrete or integrated logic circuitry. A processor may be integrated circuitry, i.e., integrated processing circuitry, and that the integrated processing circuitry may be realized as fixed hardware processing circuitry, programmable processing circuitry and/or a combination of both fixed and programmable processing circuitry. Accordingly, the terms "processing circuitry," "processor" or "controller," as used herein, may refer to any one or more of the foregoing structures or any other structure operable to perform techniques described herein.

Examples of memory 124 may include any type of computer-readable storage media. include random access memory (RAM), read only memory (ROM), programmable read only memory (PROM), erasable programmable read only memory (EPROM), one-time programmable (OTP) memory, electronically erasable programmable read only memory (EEPROM), flash memory, or another type of volatile or non-volatile memory device. In some examples the computer readable storage media may store instructions that cause the processing circuitry to execute the functions described herein. In some examples, the computer readable storage media may store data, such as configuration information, temporary values and other types of data used to perform the functions of this disclosure. Though shown as separate from processing circuitry 110 in the example of FIG. 1, in other examples, memory 124 may be on the same component, e.g., the same integrated circuit (IC) as processing circuitry 110.

Driver circuitry 114 may include switches, amplifier circuits, tuning circuitry, communication circuitry, and so on, configured to send driving signals 112 to coil 102 to generate electromagnetic field 122 per instructions from processing circuitry 110. Tuning circuitry may include one or more capacitors, inductors, or similar components. In some examples driver circuitry 114 may include logic circuitry or other processing circuitry to receive feedback signal, or communication signals from coil 102. In some examples, driver circuitry may receive instructions from processing circuitry 110 that controls the operation of driver circuitry 114.

Sensing circuitry 116 may include filter circuits, amplifier circuits, analog to digital converter (ADC), and other related circuitry to receive signals from sensors 126 and transfer the information from the sensors to processing circuitry 110. Examples of sensors 126 may include strain gauges, pressure sensors, capacitive sensors, hall sensors and or loop sensors to detect magnetic field strength, temperature sensors, and so on. Though shown as attached to coil 102 in the example of FIG. 1, one or more of sensors 126 may be located within system 100 to detect the amount of curvature or flex in any or all of coil 102, housing 106, circuit board 104 or other components of system 100. In other words, as the shape of system 100 changes, one or more deformation sensors of sensors 126 may output a signal indicating the shape or degree of deformation of system 100. The spatial relationship between the circuitry and coil 102 may change upon system 100 conforming to the surface of the external object. In some examples, one or more of sensors 126 may generate a signal representative of a spatial relationship between any of driver circuitry 114 and coil 102, processing circuitry 110 and coil 102, or other components on circuit board 104. In this disclosure, the term "driver circuitry" may include the amplifiers, switches and so on that are part of driver circuitry 114, but "driver circuitry" may also include processing circuitry 110, circuit board traces, ESD protection circuitry (not shown in FIG. 1) and other circuitry, e.g., other circuitry 118, that drives and/or controls coil 102 to generate electromagnetic field 122.

In the example in which one or more of sensors 126 is a strain gauge, the strain gauge may be configured using a Wheatstone bridge, which may minimize the effects of other environmental effects on the strain gauge, e.g., the thermal coefficient of resistance. In the example in which one or more of sensors 126 includes a capacitive sensor, the capacitive sensor may be configured to determine whether two or more layers are sliding relative to each other. In other examples, a capacitive sensor may be used to determine whether a material is under pressure and spacing near the sensor has increased or decreased.

In some examples, when coil 102 is in a first condition, e.g., undeformed, the output electromagnetic field may have a first shape, with the strength and direction of the electromagnetic field varying along the length of coil 102 and along a distance from coil 102. In the first shape, components of wireless power transmitting system 100 may be subject to a field strength at a first magnitude and direction. When system 100 is applied to a patient, e.g., near the thoracic region, and conforming to the shape of the patient's ribs, for example, coil 102 and/or housing 106, may change shape to a second shape. Changing shape may include increasing radius, decreasing radius, or a ripple shape, such as if pressed into the indention along the patient's spine. The second shape may cause a change in the electromagnetic field strength for one or more components, which may be caused by the one or more components, e.g., driver circuitry 114 or sensing circuitry 116, moving closer or farther from coil 102. The change in the electromagnetic field strength may also be caused by a changing shape of the electromagnetic field because of the change in shape of coil 102.

Applying system 102 to other patient locations, such as to the ankle, may result in a third shape, e.g., a smaller radius of coil 102 and/or housing 106, as well as circuit board 104 in some examples. Sensors 126 may output a signal indicating the change in shape. Processing circuitry 110 may receive the signal representative of a change in shape (e.g., sensor signal (voltage, current, etc.) and determine the changes in the effects of the electromagnetic field on the components based on the received signals indicating changes in the spatial relationship.

Power source 120 may comprise an electrical energy storage device that stores and provides electrical energy to the circuitry of system 100. In some examples power source 120 may include a battery, including a rechargeable battery. In other examples, power source 120 may be another type of electrical energy storage device, such as a fuel cell, capacitor and so on. In some examples, power source 120 may include a power converter, such as an AC-DC converter, DC-DC converter and so on. In some examples, system 100 may include connections external to housing 106 (not shown in FIG. 1) configured to receive external power, such as from a wall outlet, to provide power to system 100, and/or to recharge power source 120. In some examples, electromagnetic field 122 may influence the operation of power source 120. In other examples, circuitry of power source 120 may impact the loading of electromagnetic field 122 and coil 102.

In operation, processing circuitry 110 may receive from the one or more sensors of sensors 126, and via sensing circuitry 116, signals representative of the spatial relationship between the driver circuitry of system 100 and coil 102. As the spatial relationship changes, e.g., because of system 100 conforming to the shape of an external object, processing circuitry 110 may control driving circuitry 114 to adjust driving signal 112 output from the driver circuitry to coil 102 to compensate for changes in the spatial relationship between the circuitry and coil 102. Processing circuitry 110 may cause driving circuitry 114 to adjust driving signal 112 based on processing circuitry 110 interpreting the signals from sensing circuitry 116 that represent the spatial relationship between the circuitry and coil 102.

Because the power transmitting antenna, coil 102, may be implemented as a coiled conductor, coil 102 includes properties of an inductor. An inductor may include at least some resistance in addition to its inductance, e.g., because of the length of the conductor, e.g., wire. The type of material, length, cross-sectional area, and other factors may impact the amount of resistance. The lower the value of this resistance R, the better the quality of the coil. The ratio between the resistance components and the frequency-dependent inductance is the loss factor (loss factor=R/2πf L). The inverse of loss factor is the quality factor or Q-value (Q=2πf L/R=ωL/R). Here "f" is the frequency of the current flowing through coil 102, "L" is the effective inductance of the coil in Henrys and "R" is the effective resistance of the coil in Ohms. Therefore, the Q-value will differ according to the frequency. Another way to describe Q-value at the operating frequency is the ratio of reactance of coil 102 to its resistance.

In some examples, processing circuitry 110 may determine the impedance of coil 102 to calculate an estimate for the amount of heating of the power receiving unit, e.g., the secondary device, according to the following equation. In the following equations the "Q" refers to an amount of heat in units of Watts and is not the same as the Q-value described above.

$$Q_{receive} = P_{tank} - Q_{transmit} - P_{recieve\text{-}batt}$$

where:
$Q_{receive}$ The amount of heat for the receiving unit
$P_{tank}$ The power in the coil 102 and in the tuning capacitor
$Q_{transmit}$ The amount of heat for the transmitting unit
$P_{recieve\text{-}batt}$ The power received by the battery of the secondary device Processing circuitry 110 may determine the amount of heat of coil 102, according to:

$$Q_{transmit} = I_{tank}^2 \times R_{transmit}$$

where:
$Q_{transmit}$ The amount of heat, in watts, of the transmitting unit
$I_{tank}$ The current through coil 102 from driver circuitry 114
$R_{transmit}$ The AC impedance of coil 102, e.g., loading of coil 102

$Q_{transmit}$ may include any heating associated with transmitting the wireless power. In some examples, $Q_{transmit}$ may include eddy currents in the main circuit board or other circuit boards of system 100. Though shown as a single circuit board 104, the circuitry of system 100 may be split among several circuit boards, such as a separate user interface circuit board. System 100 may include other components not shown in FIG. 1, such as shielding material, ferrite material and so one that may absorb some of the transmitted energy. Eddy currents may also cause heating in, losses in ferrite, eddy currents in a battery, e.g., power source 120, or other components. Similarly, $Q_{receive}$ may include all the heats in the power receiving unit, e.g., IMD 130, including eddy currents in shielding, a header, a ground plane, rectification circuit losses, battery path impedance, and so on (not shown in FIG. 1).

The impedance of coil 102 may be affected by several factors. For example, the material, and cross-sectional area of the conductors of coil 102 may have a certain resistance per unit distance, e.g., Ohms per millimeter. Changes in temperature may also impact the resistance of a conductor based on the temperature coefficient of resistance for coil 102. Also, as described above, the spatial relationship between at least the driver circuitry and coil 102 may impact the loading of coil 102. In some examples, electromagnetic field 122 may generate eddy currents in the driver circuitry. The eddy currents in the circuitry, e.g., in the traces in circuit board 104 as well as in electrical components mounted to circuit board 104, may cause a change in a driving signal that is output from the driver circuitry to the antenna. In other words, the signal path, e.g., 112, for the driving signal may be positioned with respect to the coil 102 such that the eddy currents in the signal path may cause a change in the current magnitude, voltage magnitude or other characteristics of the driving signal. As described above, other signal paths on circuit board 104, e.g., between power source 120, processing circuitry 110, sensing circuitry 116 and so on (not shown in FIG. 1) may also be configured with respect to coil 102, such that electromagnetic field 122 may cause the driving signal output to change due to the eddy current changes at different spatial relationships between coil 102 and the circuitry. A mathematical model for the transmit coil impedance may be based on the tank current ($I_{tank}$), the coil temperature, the driver signal frequency (f), which impacts the Q-value, and the spatial relationship between coil 102 and the circuitry as measured by the degree of deformation. Therefore, the impedance of coil 102 may be described according to:

$$R_{transmit} = A + B \times I_{tank} + C \times T_{transmit} + D \times \text{Deformation}$$

where:
$T_{transmit}$ The temperature of coil 102
$I_{tank}$ The current through coil 102 from driver circuitry 114
$R_{transmit}$ The total AC impedance of coil 102
Deformation The deformation based on sensors 126
A A coefficient based on the resistance of the coil
B A coefficient for the coil current
C A coefficient for the coil temperature
D A coefficient for the coil deformation In some examples, the coefficient "A" may be based on zero tank current ($I_{tank}$), nominal temperature, and nominal deformation or position. In some examples, processing circuitry 110 may adjust the amount of power output by coil 102 to ensure the estimated temperature stays within a predetermined temperature range. In the example of an implantable medical device, should the temperature of the medical device rise above a predetermined temperature threshold, the tissue around the medical device may become uncomfortable for a patient. In other examples, the power receiving device may include circuitry that is sensitive to temperatures outside of the predetermined range.

Figure 2:
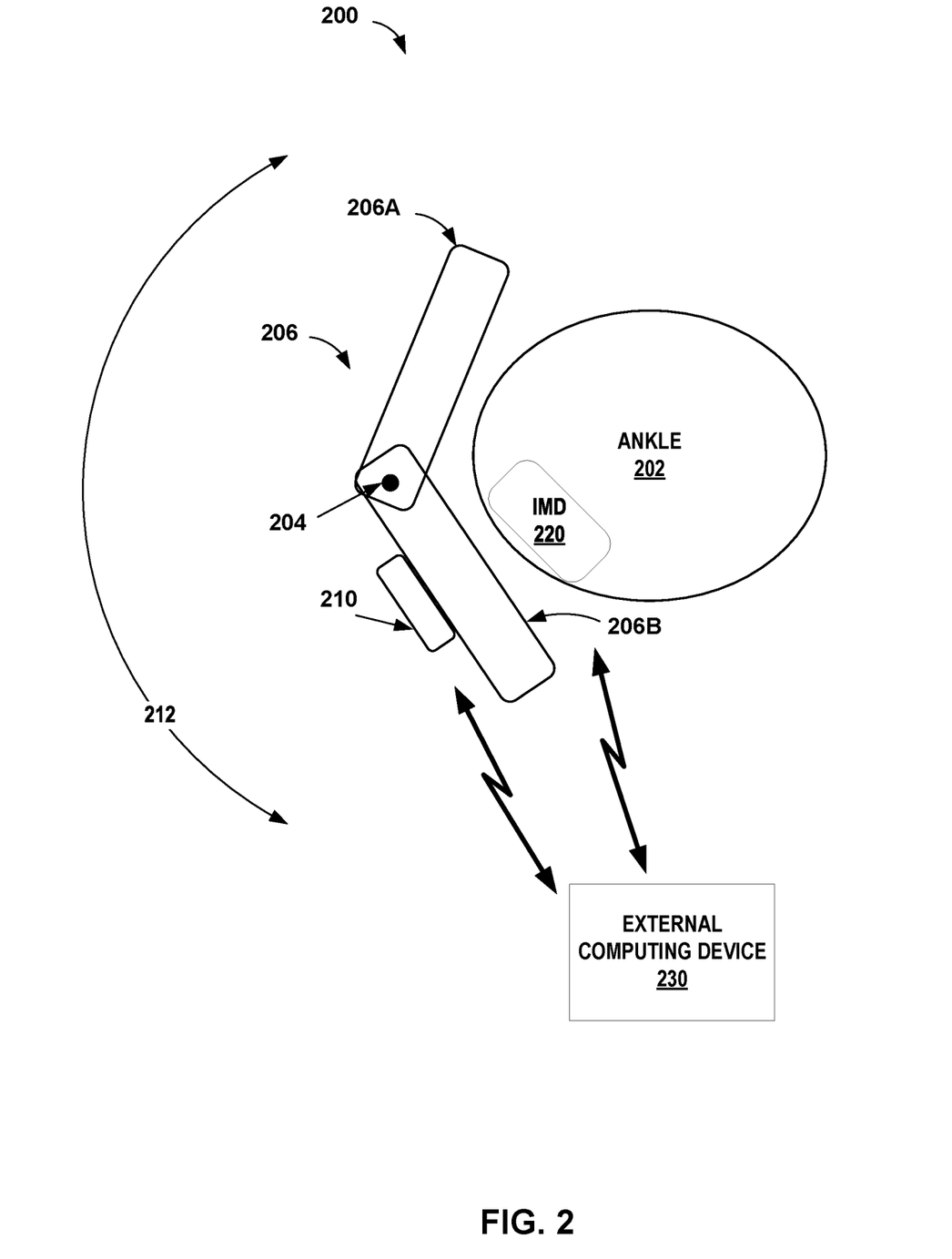
FIG. 2 is a conceptual diagram illustrating power transmitting system with a hinged coil and an implantable power receiving device according to one or more techniques of this disclosure.

FIG. 2 is a conceptual diagram illustrating power transmitting system with a hinged coil 206 and an implantable power receiving device such as IMD 220 according to one or more techniques of this disclosure. System 200 is an example of system 100 described above in relation to FIG. 1 and may have the same or similar functions and characteristics as system 100.

In the example of FIG. 2, system 200 includes a hinged coil 206, including hinge 204 and two hinged portions 206A and 206B, driving circuitry 210, and a power receiving device, IMD 220 implanted near an ankle 202 of a patient, and an external computing device 230. As described above in relation to FIG. 1, driving circuitry 210 may cause coil 206 to generate an electromagnetic field that may transfer power to IMD 220. In some examples, hinged coil 206 may be similar to system 100 of FIG. 1 and include a power supply and other similar components for generating energy that can be delivered to IMD 220. Although FIG. 2 describes hinged coil 206 being located near ankle 202, hinged coil 206 may be configured to be applied near any anatomical portion of the patient within which IMD 220 is implanted.

IMD 220 may be a medical device implanted near ankle 202 of a patient to sense bioelectrical signals or movement signals and/or to provide electrical stimulation therapy to the patient. IMD 220 may include processing circuitry, sense circuitry, communication circuitry and other components. A housing of IMD 220 may enclose the circuitry, and other components, of IMD 220 to protect IMD 220 from bodily fluids, shock, impact and so on. In some examples, IMD 220 may include a receiving coil, an electrical energy storage device and charging circuitry (not shown in FIG. 2) configured to receive the power and recharge the electrical energy storage device of IMD 220. In this disclosure, hinged coil 206 may also be described as charging coil 206. System 200 may also be described as transcutaneous power transfer and charging system.

FIG. 2 depicts hinged coil 206 with two coil portions 206A and 206B with a single hinge 204. In other examples, hinged coil 206 may include two or more hinges and three or more coil portions. In other examples, hinged coil 206 may include two or more separate coils and the separate coils may be rigid or flexible. In some examples, a single driver circuit in driver circuitry 210 may provide each separate coil the driving signal that generates the electromagnetic field. In other examples, a separate driver circuit in driver circuitry 210 (not shown in FIG. 2) may provide a respective driving signal for each respective coil. For example, driver circuitry 210 may drive a first coil at a first output magnitude and frequency and drive a second coil at the same or different output magnitude and frequency. In some examples, the driving signal for the first coil may be out of phase in relation to the driving signal for the second coil. By controlling the phase angle, frequency and magnitude, driver circuitry 210 may focus or disperse the electromagnetic energy delivered by two or more charging coils.

As system 200 conforms to ankle 202, radius 212 may change and the spatial relationship between driver circuitry 210 and hinged coil 206 may change. As described above in relation to FIG. 1, system 200 may include one or more sensors, including sensors (not shown in FIG. 2) that are configured to generate a signal representative of a spatial relationship between driver circuitry 210 and hinged coil 206. In some examples the sensors may be located near hinge 204 and may detect changes in radius 212, e.g., based on movement between fingers of a capacitive sensor, the amount of strain on a strain gauge, the pressure on an element of system 200, and so on.

As described above in relation to FIG. 1, driver circuitry 210 may include processing circuitry (not shown in FIG. 2) that may receive from the one or more sensors, the amount of strain, or other signal representative of radius 212, and thereby the spatial relationship between driver circuitry 210 and the hinged coil 206. The processing circuitry may adjust the driving signal output from driver circuitry 210 to hinged coil 206 based on the signal representative of radius 212.

The adjustments may compensate for changes in the electromagnetic field output to IMD 220 because of changes in loading on hinged coil 206, as described above in relation to FIG. 1. For example, processing circuitry 210 may receive communication from IMD 220 providing an indication of the power received (e.g., $P_{recieve\text{-}batt}$) by a battery, or other electrical energy storage device of IMD 220 (not shown in FIG. 2). The processing circuitry of system 200 may use the received indication to determine the transmit coil impedance of hinged coil 206. In some examples, driving circuitry 210 may communicate directly with IMD 220. In other examples, external computing device 230 may receive the indication of the power received from IMD 220 and further communicate with driver circuitry 210 to send the indication of the power received. In some examples, the processing circuitry of driver circuitry 210 may adjust the amount of power output by hinged coil 206 to ensure an estimated temperature of IMD 220, e.g., of the housing of IMD 220, stays within a predetermined temperature range.

Figure 3A:
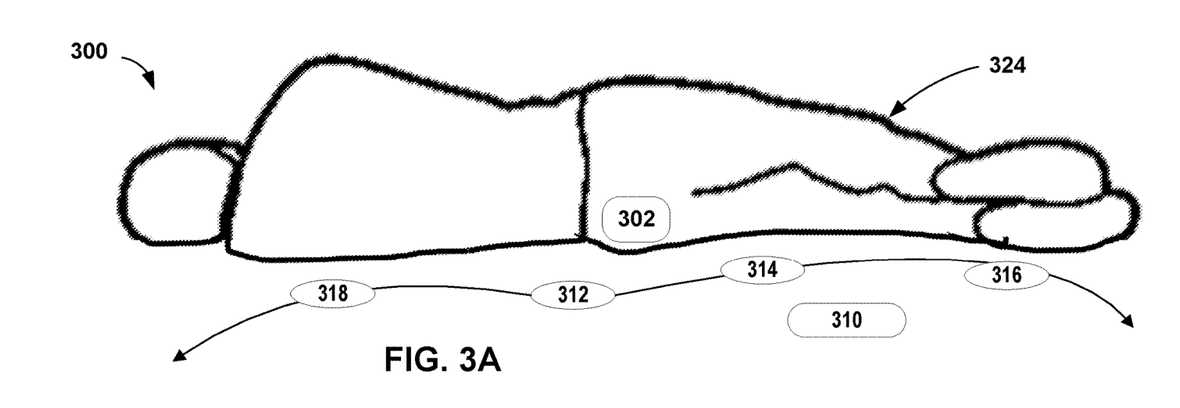
FIGS. 3A and 3B are conceptual diagrams illustrating an example wireless power transmitting system including multiple charging coils, according to one or more techniques of this disclosure.
Figure 3B:
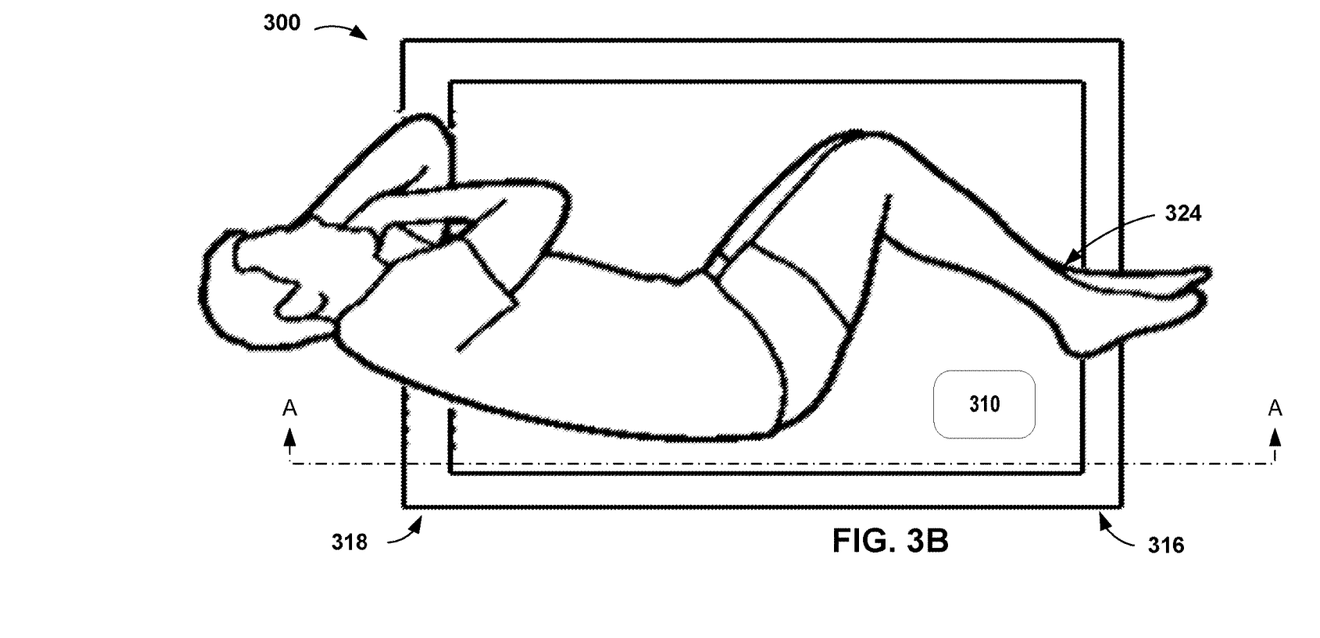

FIGS. 3A and 3B are conceptual diagrams illustrating an example wireless power transmitting system including multiple charging coils, according to one or more techniques of this disclosure. System 300 is an example of systems 100 and 200 described above in relation to FIGS. 1 and 2 and may have the same or similar functions and characteristics as systems 100 and 200. FIG. 3A represents an A-A sectional view of FIG. 3B.

FIG. 3A illustrates patient 324 with power receiving device 302 lying on a flexible wireless power transmitting system 300 including coils, depicted by 312, 314, 316 and 318, and driver circuitry 310. Power transmitting system 300 may generate one or more electromagnetic fields to wireless transfer power to power receiving device 302. In some examples, power receiving device 302 may be an implantable medical device, such as IMD 220 of FIG. 2. In other examples, power receiving device 302 may be a wearable medical device, or other portable electronic device, such as a mobile phone, music player, fitness tracker and so on. Though shown as implanted in the buttock area, or located in a hip pocket of patient 324, in other examples, power receiving device 302 may be located in the pectoral area, near the clavicle, ankle, or any other location on patient 324.

The example of FIGS. 3A and 3B depict power transmitting system 300 as a mat or bed in which patient 324 is positioned. In other examples, power transmitting system 300 may be installed in a chair, the seat of an automobile, or other vehicle, and other similar locations. FIG. 3A is an example cross section view and FIG. 3B is a top view of a charging coil system 300 of this disclosure. Coil cross-sections 312, 314, 316 and 318 may be implemented as multiple loops of a single coil, in some examples. In other examples, coil cross-sections 312, 314, 316 and 318 may depict separate overlapping coils, or separate coils that do not overlap.

Similar to the description above with respect to FIGS. 1 and 2, driver circuitry 310 may include processing circuitry, coil driving amplifier circuits, tuning circuits, communication circuits, sensing circuitry including filters, amplifiers and so on connected to one or more sensors, along with other circuitry not specifically listed (not shown in FIG. 3). Driver circuitry 310 may drive each of the one or more coils of system 300 together or separately. As described above in relation to FIG. 2, the processing circuitry may control the phase angle, frequency, magnitude, and other characteristics of the driving signal to focus, or to broaden, the electromagnetic field generated by the one or more coils.

In some examples, system 300 may include a single coil, as shown in the example of FIG. 3B. In other examples, system 300 may include multiple coils. In some examples, system 300 may include a first coil near the upper body of patient 324 formed by 312 and 318, along with a second coil near the legs of patient 324 formed by 314 and 316. In other examples, system 300 may include overlapping coils, e.g., a first coil formed by 314 and 318 near the upper body of patient 324 and a second coil formed by 312 and 316 near the lower body of patient 324. In other examples, system 300 may include three or more charging coils, which may be arranged as overlapping or adjacent coils. The portions of the coils indicated by 312 and 314 are not shown in FIG. 3B.

As described above in relation to FIGS. 1 and 2, driving circuitry 310 may be located such that the charging coils of system 300 may generate the electromagnetic field that encompasses the processing circuitry, the driver circuitry, and the one or more sensors (not shown in FIG. 3). The one or more sensors may include temperature sensors to provide temperature measurements for the one or more charging coils, e.g., $T_{transmit}$ as described above in relation to FIG. 1. Other sensors may generate a signal representative of a spatial relationship between driver circuitry 310 and the one or more charging coils. For example, when patient 324 sits or lies down near driver circuitry 310, the components of system 300 may conform to the surface of patient 324. The spatial relationship between driver circuitry 310 and the coils may change as patient 324 moves. For example, the coils depicted by 314 and 316 may compress and move closer to driver circuitry 310. Changes in the shape and angle of the charging coils may cause changes in the electromagnetic field surrounding driver circuitry 310 and causes changes in the driving signal and operation of the processing circuitry. Based on indications from strain gauges, capacitive sensors, pressure sensors or other sensors, the processing circuitry of driver circuitry 310 may determine the changes in the spatial relationship and cause adjustments to the driving signal that may compensate for the changes in the driving signal caused by the changes in the spatial relationship.

Figure 4:
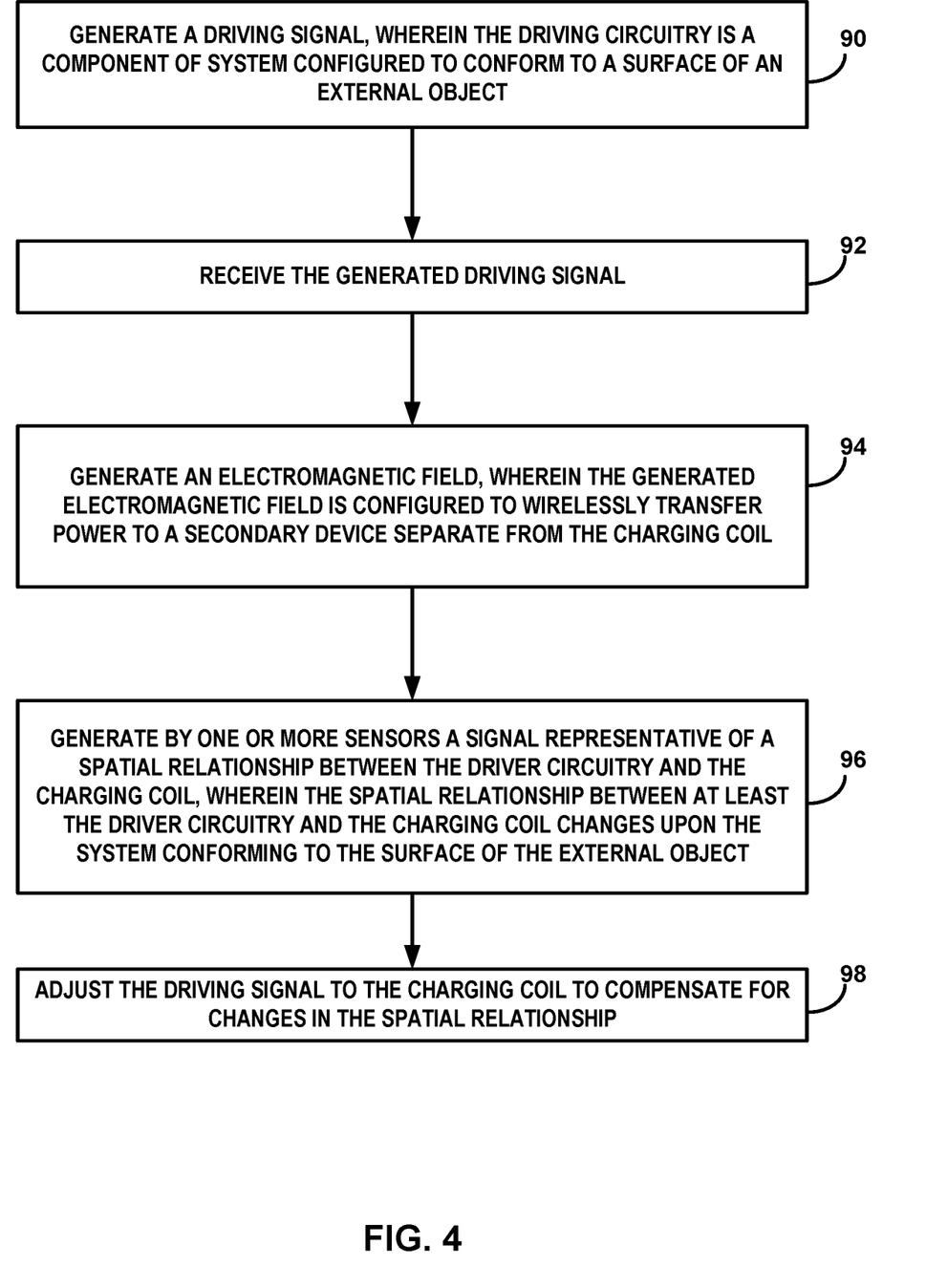
FIG. 4 is a flowchart illustrating an example operation of the wireless power transmitting system of this disclosure.

FIG. 4 is a flowchart illustrating an example operation of the wireless power transmitting system of this disclosure. The blocks of FIG. 4 will be described in terms of FIG. 1, unless otherwise noted, however other example system may perform the same or similar functions.

In the example of FIG. 4, processing circuitry 110 may execute instructions stored at memory 124 to cause driving circuitry 114 to generate driving signal 112 (90). Driving circuitry 114, processing circuitry 110, and other components on circuit board 104 are components of system 100. As described above in relation to FIG. 1, housing 106, and in some examples coil 102, circuitry board 104 and other components of system 100 may be configured to conform to another surface of furniture, anatomy of a patient, or other object external to housing 106.

Coil 102 may receive the generated driving signal 112 from driving circuitry 114 (92) and generate an electromagnetic field 122 (94). As described above in relation to FIGS. 1-3, generated electromagnetic field 122 may wirelessly transfer power to a secondary device separate from the charging coil such as IMD 220 or some other power receiving unit 302.

Processing circuitry 110 may receive, via sensing circuitry 116, signals generated by one or more sensors 126. Signals from temperatures sensors may provide an indication of $T_{transmit}$, e.g., the temperature of primary coil 102. Other sensors, such as one or more deformation sensors may output a signal representative of the spatial relationship between driver circuitry (e.g., any circuitry on circuit board 104) and charging coil 102 (96). As described above in relation to FIGS. 1-3, the spatial relationship between at least the driver circuitry and the charging coil may change upon system 100 conforming to the surface of the external object. Changes in the spatial relationship may cause changes in $R_{transmit}$, e.g., the total AC impedance of coil 102, and therefore changes in the electromagnetic field generated by coil 102. Processing circuitry 110 then controls driver circuitry 114 to adjust driving signal 112 to charging coil 102 to compensate for changes in the spatial relationship (98).

In one or more examples, the functions described above may be implemented in hardware, software, firmware, or any combination thereof. For example, the various components of FIGS. 1-3, such as processing circuitry 110, driver circuitry 210, IMD 220, and driver circuitry 310, may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

The term "non-transitory" may indicate that the storage medium is not embodied in a carrier wave or a propagated signal. In certain examples, a non-transitory storage medium may store data that can, over time, change (e.g., in RAM or cache). By way of example, and not limitation, such computer-readable storage media, may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or other computer readable media. In some examples, an article of manufacture may include one or more computer-readable storage media.

Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Combinations of the above should also be included within the scope of computer-readable media.

Instructions may be executed by one or more processors, such as one or more DSPs, general purpose microprocessors, ASICs, FPGAs, or other equivalent integrated or discrete logic circuitry. Accordingly, the term "processor," as used herein, such as processing circuitry 110, may refer to any of the foregoing structure or any other structure suitable for implementation of the techniques described herein. Also, the techniques could be fully implemented in one or more circuits or logic elements.

The techniques of this disclosure may be implemented in a wide variety of devices or apparatuses, including, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

The techniques of this disclosure may also be described in the following examples.

Example 1: A system that includes a charging coil configured to wirelessly charge a secondary device, wherein the system is configured to conform to a surface of an external object; driver circuitry configured to operatively connect to the charging coil; and one or more sensors configured to generate a signal representative of a spatial relationship between at least the driver circuitry and the charging coil, wherein the spatial relationship between at least the driver circuitry and the charging coil changes upon the system conforming to the surface of the external object.

Example 2: The system of example 1, wherein changes in the spatial relationship change an amount of loading from the charging coil reflected to the driver circuitry.

Example 3: The system of any combination of examples 1 and 2, wherein the charging coil produces an electromagnetic field and wherein the amount of loading reflected to the driver circuitry is caused by materials within the produced electromagnetic field.

Example 4: The system of any combination of examples 1 through 3, wherein the materials within the electromagnetic field comprise one or more of metallic materials and ferromagnetic materials.

Example 5: The system of any combination of examples 1 through 4, wherein the spatial relationship between at least the driver circuitry and the charging coil is based on an amount of deformation of the charging coil.

Example 6: The system of any combination of examples 1 through 5, wherein the charging coil produces an electromagnetic field that generates eddy currents in the driver circuitry, and wherein the eddy currents cause a change in a driving signal that is output from the driver circuitry to the charging coil.

Example 7: The system of any combination of examples 1 through 6, wherein the generated signal is representative of a spatial relationship between at least the driver circuitry and the charging coil, wherein the spatial relationship between at least the driver circuitry and the charging coil changes upon the system conforming to the surface of the external object.

Example 8: The system of any combination of examples 1 through 7, further includes conform to the surface of the external object; and enclose the driver circuitry, wherein a change in the shape of the conformable housing causes a change in the spatial relationship between the driver circuitry and the charging coil.

Example 9: The system of any combination of examples 1 through 8, further includes receive, from the one or more sensors, the signal representative of the spatial relationship between at least the driver circuitry and the charging coil; control, based on the signal representative of the spatial relationship between the driver circuitry and the charging coil, the driving circuitry to adjust a driving signal output from the driver circuitry to the charging coil to compensate for changes in the spatial relationship between the driver circuitry and the charging coil.

Example 10: The system of any combination of examples 1 through 9, wherein the charging coil is configured to generate an electromagnetic field that encompasses the processing circuitry, the driver circuitry, and the one or more sensors, wherein electromagnetic field causes changes in the driving signal and operation of the processing circuitry, and wherein the adjustment by the processing circuitry of the driving signal compensates for the changes in the driving signal caused by different positions within the electromagnetic field indicated by the spatial relationship.

Example 11: The system of any combination of examples 1 through 10, wherein the processing circuitry is configured to determine a temperature of the secondary device.

Example 12: The system of any combination of examples 1 through 11, wherein the processing circuitry is configured to determine changes in the temperature of the secondary device based on the amount of deformation of the charging coil.

Example 13: The system of any combination of examples 1 through 12, wherein the secondary device is an implantable medical device.

Example 14: The system of any combination of examples 1 through 13, wherein the charging coil comprises a flexible coil.

Example 15: The system of any combination of examples 1 through 14, wherein the charging coil comprises a hinged coil.

Example 16: The system of any combination of examples 1 through 15, wherein charging coil comprises a plurality coils; and wherein each coil of the plurality of coils connect together by a hinge portion or by a flexible portion.

Example 17: A device that includes driver circuitry configured to: operatively connect to an antenna; output a driving signal to the antenna, wherein the driving signal causes the antenna to output an electromagnetic field configured to wirelessly transfer energy to a secondary device and wherein the antenna configured to conform to a surface of an external object; processing circuitry operatively coupled to the driver circuitry, the processing circuitry configured to: receive, from the one or more sensors, the signal representative of a spatial relationship between the driver circuitry and the antenna; control, based on the signal representative of the spatial relationship between the driver circuitry and the charging coil, the driving circuitry to adjust the driving signal to compensate for changes in the spatial relationship between the driver circuitry and the antenna.

Example 18: The device of example 17, wherein the signal from the one or more sensors is representative of a spatial relationship between at least the driver circuitry and the antenna, wherein the spatial relationship between at least the driver circuitry and the antenna changes upon the system conforming to the surface of the external object.

Example 19: The device of any combination of examples 17 and 18, wherein the electromagnetic field generates eddy currents in the driver circuitry and the processing circuitry, and wherein the eddy currents cause a change in the driving signal that is output to the antenna.

Example 20: The device of any combination of examples 17 through 19, further comprising a conformable housing configured to enclose the driver circuitry, wherein a change in the shape of the conformable housing causes a change in the spatial relationship between the driver circuitry and the antenna.

Example 21: The device of any combination of examples 17 through 20, wherein the processing circuitry is configured to determine a temperature of the secondary device.

Example 22: The device of any combination of examples 17 through 21, wherein the spatial relationship between the driver circuitry and the charging coil is based on an amount of deformation of the antenna.

Example 23: The device of any combination of examples 17 through 22, wherein the processing circuitry is configured to determine changes in a temperature of the secondary device based on the amount of deformation of the antenna.

Example 24: The device of any combination of examples 17 through 23, wherein the secondary device is an implantable medical device.

Example 25: The device of any combination of examples 17 through 24, wherein the processing circuitry is configured to determine an amount of heating in the device.

Example 26: A method includes generating, by driver circuitry, a driving signal, wherein the driving circuitry is a component of system configured to conform to a surface of an external object; receiving, by a charging coil, the generated driving signal; generating, by the charging coil and based on the driving signal, an electromagnetic field, wherein the generated electromagnetic field is configured to wirelessly transfer power to a secondary device separate from the charging coil; generating, by one or more sensors a signal representative of a spatial relationship between the driver circuitry and the charging coil, wherein the spatial relationship between at least the driver circuitry and the charging coil changes upon the system conforming to the surface of the external object.

Example 27: The method of example 26, wherein the generated signal is also representative of a spatial relationship between at least the driver circuitry and the charging coil, and wherein the spatial relationship between at least the driver circuitry and the charging coil changes upon the system conforming to the surface of the external object.

Example 28: The method of any combination of examples 26 and 27, wherein the electromagnetic field generates eddy currents in the driver circuitry and wherein the eddy currents cause a change in a driving signal that is output from the driver circuitry to the charging coil.

Example 29: The method of any combination of examples 26 through 28, further comprising receiving, by processing circuitry of the system, the signal representative of the spatial relationship between at least the driver circuitry and the charging coil from the one or more sensors; controlling, by the processing circuitry, the driving circuitry to adjust the driving signal output from the driver circuitry to the charging coil to compensate for changes in the spatial relationship between the driver circuitry and the charging coil based on the received signal representative of the spatial relationship between the driver circuitry and the charging coil.

Example 30: The method of any combination of examples 26 through 29, further comprising, determining a temperature of the secondary device based on the spatial relationship between the driver circuitry and the charging coil.

Example 31: The method of any combination of examples 26 through 30, wherein transferring power to a secondary device comprises transferring power to an implantable medical device, wherein the transferred power charges an electrical energy storage device of the implantable medical device.

Various examples of the disclosure have been described. These and other examples are within the scope of the following claims.

What is claimed is:

1. A system comprising:
    a charging coil configured to wirelessly charge a secondary device, wherein the system is configured to conform to a surface of an external object;
    driver circuitry configured to operatively connect to the charging coil and output a driving signal to the charging coil;
    one or more sensors configured to generate a signal representative of a spatial relationship between at least the driver circuitry and the charging coil, wherein the spatial relationship between at least the driver circuitry and the charging coil changes upon the system conforming to the surface of the external object; and
    processing circuitry configured to control, based on the signal representative of the spatial relationship, the driver circuitry to adjust the driving signal output to the charging coil.

2. The system of claim 1, wherein changes in the spatial relationship change an amount of loading from the charging coil reflected to the driver circuitry.

3. The system of claim 1, wherein the charging coil produces an electromagnetic field and wherein the amount of loading reflected to the driver circuitry is caused by materials within the produced electromagnetic field.

4. The system of claim 3, wherein the materials within the electromagnetic field comprise one or more of metallic materials and ferromagnetic materials.

5. The system of claim 1, wherein the spatial relationship between at least the driver circuitry and the charging coil is based on an amount of deformation of the charging coil.

6. The system of claim 1, further comprising a housing configured to:
    conform to the surface of the external object; and
    enclose the driver circuitry, wherein a change in the shape of the conformable housing causes a change in spatial relationship between the driver circuitry and the charging coil.

7. The system of claim 1, wherein the processing circuitry is configured to:
    receive, from the one or more sensors, the signal representative of the spatial relationship between at least the driver circuitry and the charging coil;
    determine, based on the signal representative of the spatial relationship, an adjusted driving signal to compensate for changes in the spatial relationship between the driver circuitry and the charging coil; and
    control the driving circuitry to output the adjusted driving signal to the charging coil.

8. The system of claim 7,
    wherein the charging coil is configured to generate an electromagnetic field that encompasses the processing circuitry, the driver circuitry, and the one or more sensors,
    wherein electromagnetic field causes changes in the driving signal and operation of the processing circuitry, and
    wherein the adjusted driving signal compensates for the changes in the driving signal caused by changed locations of at least one of the processing circuitry or the driver circuitry within the electromagnetic field as indicated by the spatial relationship.

9. The system of claim 1,
    wherein the processing circuitry is configured to determine a temperature of the secondary device, and wherein the processing circuitry is configured to determine changes in the temperature of the secondary device based on an amount of deformation of the charging coil indicated by the signal.

10. The system of claim 9, wherein the secondary device is an implantable medical device.

11. The system of claim 1, wherein the charging coil comprises a flexible coil.

12. The system of claim 1, wherein the charging coil comprises a hinged coil.

13. The system of claim 1,
wherein the charging coil comprises a plurality coils; and
wherein each coil of the plurality of coils connect together by a hinge portion or by a flexible portion.

14. A device comprising:
driver circuitry configured to:
operatively connect to an antenna;
output a driving signal to the antenna,
wherein the driving signal causes the antenna to output an electromagnetic field configured to wirelessly transfer energy to a secondary device and
wherein the antenna configured to conform to a surface of an external object;
processing circuitry operatively coupled to the driver circuitry, the processing circuitry configured to:
receive, from one or more sensors, a signal representative of a spatial relationship between the driver circuitry and the antenna;
control, based on the signal representative of the spatial relationship between the driver circuitry and the antenna charging coil, the driving circuitry to adjust the driving signal out to the antenna to compensate for changes in the spatial relationship between the driver circuitry and the antenna.

15. The device of claim 14, wherein the signal from the one or more sensors is representative of a spatial relationship between at least the driver circuitry and the antenna, wherein the spatial relationship between at least the driver circuitry and the antenna changes upon the system conforming to the surface of the external object.

16. The device of claim 14, wherein the processing circuitry is configured to determine changes in a temperature of the secondary device based on an amount of deformation of the antenna indicated by the signal.

17. The device of claim 14, wherein the secondary device is an implantable medical device.

18. The device of claim 14, wherein the processing circuitry is configured to determine an amount of heating in the secondary device.

19. A method comprising:
generating, by driver circuitry, a driving signal, wherein the driving circuitry is a component of system configured to conform to a surface of an external object;
receiving, by a charging coil, the generated driving signal;
generating, by the charging coil and based on the driving signal, an electromagnetic field, wherein the generated electromagnetic field is configured to wirelessly transfer power to a secondary device separate from the charging coil;
generating, by one or more sensors, a signal representative of a spatial relationship between the driver circuitry and the charging coil, wherein the spatial relationship between at least the driver circuitry and the charging coil changes upon the system conforming to the surface of the external object; and
controlling, by processing circuitry and based on the signal representative of the spatial relationship, the driver circuitry to adjust the driving signal output to the charging coil.

20. The method of claim 19, further comprising:
determining, by the processing circuitry, a temperature of the secondary device, and
determining, by the processing circuitry, changes in the temperature of the secondary device based on an amount of deformation of the charging coil indicated by the signal.

* * * * *